US 8,476,067 B2
Jul. 2, 2013

(12) United States Patent
Morgan

(10) Patent No.: US 8,476,067 B2
(45) Date of Patent: Jul. 2, 2013

(54) PHOTOBIOREACTOR AND METHOD FOR PROCESSING POLLUTED AIR

(75) Inventor: Robert Morgan, Palm Desert, CA (US)

(73) Assignee: Phyco2 LLC, Santa Maria, CA (US)

( * ) Notice: Subject to any disclaimer, the term of this patent is extended or adjusted under 35 U.S.C. 154(b) by 546 days.

(21) Appl. No.: 12/526,151

(22) PCT Filed: Feb. 1, 2008

(86) PCT No.: PCT/US2008/052801
§ 371 (c)(1),
(2), (4) Date: Aug. 6, 2009

(87) PCT Pub. No.: WO2008/097845
PCT Pub. Date: Aug. 14, 2008

(65) Prior Publication Data
US 2010/0261260 A1    Oct. 14, 2010

Related U.S. Application Data

(60) Provisional application No. 60/899,662, filed on Feb. 6, 2007.

(51) Int. Cl.
C12M 1/00 (2006.01)
C12M 1/04 (2006.01)

(52) U.S. Cl.
USPC .................. 435/292.1; 435/293.2; 435/296.1

(58) Field of Classification Search
USPC ................................. 435/292.1, 293.2, 296.1
See application file for complete search history.

(56) References Cited

U.S. PATENT DOCUMENTS

| 286,613 A | 10/1883 | Howland |
| 4,676,956 A | 6/1987 | Mori |
| 5,137,828 A | 8/1992 | Robinson et al. |
| 6,416,993 B1 * | 7/2002 | Wexler et al. ............ 435/262.5 |
| 2003/0073231 A1 | 4/2003 | Dutil |
| 2003/0228684 A1 | 12/2003 | Burbidge et al. |
| 2006/0270036 A1 * | 11/2006 | Goodwin et al. ............ 435/395 |
| 2007/0092962 A1 | 4/2007 | Sheppard |

FOREIGN PATENT DOCUMENTS

| EP | 0935991 | 8/1999 |
| GB | 2118572 | 11/1983 |
| JP | 2002-315569 A | 10/2002 |
| WO | 99/15620 A1 | 4/1999 |
| WO | 2007129327 | 11/2007 |

OTHER PUBLICATIONS

European Search Report for EP 08 72 8827 dated Dec. 8, 2011.
Gammack, David et al. "Flow in pipes with non-uniform curvature and torsion", J. Fluid Mech. (2001), vol. 433, pp. 357-382.
Morita, Masahiko "Photosynthetic Productivity of Conical Helical Tubular Photobioreactor Incorporating Chlorella sorokiniana Under Field Conditions", Biotechnology and Bioengineering, vol. 77, No. 2, 2002 pp. 155-162.

* cited by examiner

Primary Examiner — Rosanne Kosson
(74) Attorney, Agent, or Firm — Fitch, Even, Tabin & Flannery LLP

(57) ABSTRACT

A photobioreactor (100) for use in treating polluted air and producing biomass may comprise, at least in part, a generally vertical tube or fluidic pathway (102), a generally vertical helical tube or fluidic pathway (104) having a light source (106) partially positioned within the helical fluidic pathway (104), a head cap assembly (108), and a base assembly (110). In one illustrative example, the light source (106) may be a light emitting diode (LED) or a plurality of light emitting diodes (LEDs). By one approach, a gas diffusion apparatus (112) is located at the base assembly (110) adjacent the generally vertical fluidic pathway (102).

16 Claims, 10 Drawing Sheets

US 8,476,067 B2

PHOTOBIOREACTOR AND METHOD FOR PROCESSING POLLUTED AIR

CROSS-REFERENCE TO RELATED APPLICATIONS

This application is a national phase application of International Application No. PCT/US2008/052801, filed Aug. 6, 2009, designating the United States and claiming priority to U.S. Patent Application No. 60/899,662, filed Feb. 6, 2007, both of which are incorporated by reference herein in their entirety.

TECHNICAL FIELD

This invention relates generally to photobioreactors, and more particularly to algal photobioreactors suitable for use in sequestering harmful emissions and producing biomass.

BACKGROUND

Bioreactors, including photobioreactors using the principles of photosynthesis, are well known in the art. Photobioreactors use photosynthetic organisms such as algae in a liquid medium along with light energy (whether synthetic light or natural sunlight) and carbon dioxide to create chemical energy from light energy while sequestering carbon dioxide. These systems may have open channels such as ponds or closed channels such as cylindrical vessels. Some systems employ tubes of a variety of sizes.

Due to a raised awareness and interest in energy independence and the Earth's climate, there is an increased demand for renewable fuels, decreasing harmful emissions or flue gasses such as those emitted from coal fired power plants, and for achieving these goals in an efficient and effective manner. In addition to the carbon dioxide emitted from electric power plants, which are some of the biggest producers of such gases, other sources of harmful emissions include manufacturing facilities and diesel power generation plants, to note but a few. It is also desirable to remove certain nitrogen oxides and sulfur oxides from flue gasses as well as carbon dioxide. For the pollutant sequestration process to be economically feasible and environmentally responsible, the process should, among other requirements, not consume more energy than it creates, be operable and effective on a substantial production scale, and should not displace crops from farmland or pastures from grassland, to note but a few.

The open channel photobioreactors, such as ponds, have faced difficulties from contamination by hostile species or external pollutants and from the inefficient use of light that illuminates only the top portion of the pond. As a more efficient photobioreactor will have an illumination surface area per unit volume (S/V) ratio that is high, shallow ponds are the norm. This, however, greatly increases land space requirements for pond-based photobioreactors. In addition, when these ponds use natural sunlight the process is limited by the available hours of sunlight. Such processing limitations can be important if the photobioreactors are used to process waste gasses from polluting facilities that operate twenty-four hours a day. Further, if these ponds are not insulated from the elements such as seasonal changes in weather, the photosynthetic organisms must be remarkably hardy to withstand changes in temperature, external pollution, and attack from hostile species.

Another approach that has received considerable attention is the closed channel system such as those systems having cylindrical tubes that employ the air lift principle. In general, air lift photobioreactors have photosynthetic material such as algae suspended in a liquid medium into which air or gas is injected into the bottom of the system which then rises through the fluid medium in the cylindrical tube.

Conventional air lift photobioreactors, however, suffer from the lack of flow patterns that can be duplicated, controlled, or even easily defined. By one approach, straight, vertical, concentric tubular containers receive the gases at an inner tube, which creates an annular liquid flow upwards through the inner tube and downwards in a space between itself and another tube. Fluid flow is important to controlling the progression of the photosynthetic stages: light-dependent reactions and light-independent reactions. Difficulty controlling the mixing properties may lead to poor photomodulation, low mass transfer coefficients, and low productivity. In addition, systems having uncontrolled or poorly controlled fluid flow or mixing properties may experience algae pooling or buildup along with damage to the photosynthetic organism that results in poor algal growth.

BRIEF DESCRIPTION OF THE DRAWINGS

The above needs are at least partially met through provision of the Photobioreactor and Method for Processing Polluted Air described in the following detailed description, particularly when studied in conjunction with the drawings, wherein.

Figure 1:
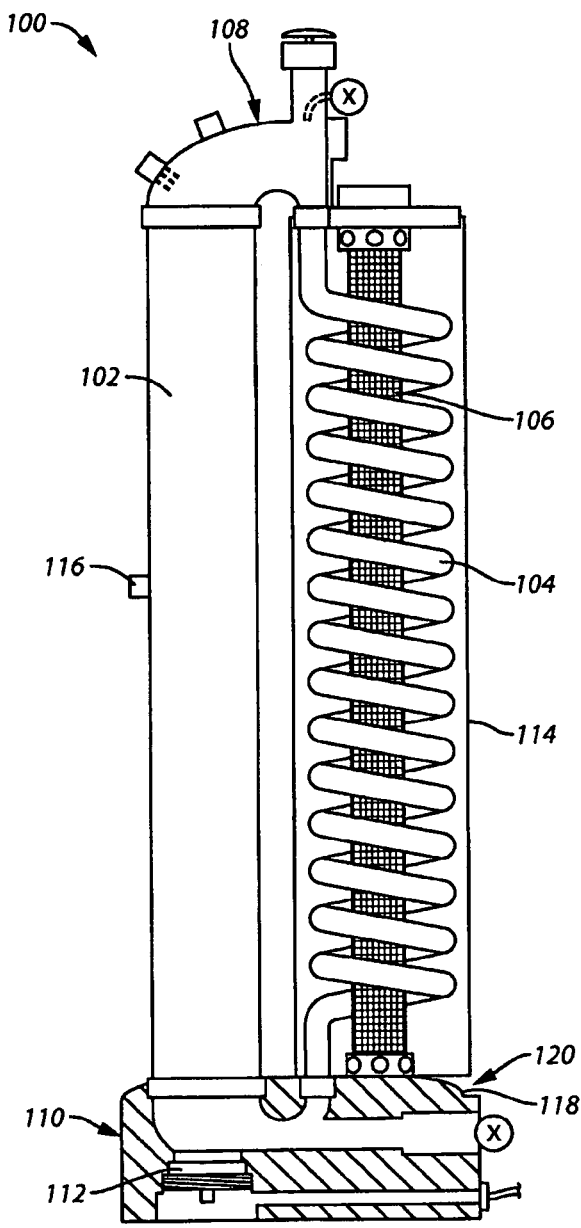
FIG. 1 comprises a front view of a photobioreactor as configured in accordance with various embodiments of the invention.

Skilled artisans will appreciate that elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention. It will further be appreciated that certain actions and/or steps may be described or depicted in a particular order of occurrence while those skilled in the art will understand that such specificity with respect to sequence is not actually required. It will also be understood that the terms and expressions used herein have the ordinary technical meaning as is accorded to such terms and expressions by persons skilled in the technical field as set forth above except where different specific meanings have otherwise been set forth herein.

BRIEF SUMMARY

Generally speaking, pursuant to these various embodiments, a photobioreactor is disclosed herein having a generally vertical fluidic pathway and a generally vertical helically shaped fluidic pathway. As used herein, the generally vertical helically shaped pathway is vertical in that the fluid medium moving within the pathway is displaced over a substantially vertical distance. The two fluidic pathways are fluidly connected by a head cap assembly and a base assembly such that a biologically active material is able to move fluidly, without substantial impediment, back and forth between the generally vertical fluidic pathway and the generally vertical helically shaped fluidic pathway.

By one approach, a light source is at least partially positioned inside a portion of the generally vertical helically shaped fluidic pathway. The light source may be a light emitting diode (LED). By one approach, this light source can comprise a plurality of light emitting diodes (LEDs). Further, the wavelengths emitted from the light source may be in the range of visible light, more particularly, between about 400 to about 700 nm. By one approach, the fluidic pathway is shaped to provide for a Dean vortex flow that gives rise to a traveling wave.

So configured and arranged, those skilled in the art will recognize that these teachings will provide for a photobioreactor that is highly effective and efficient at processing harmful emissions, sequestering carbon dioxide, and producing a biomass. Further, the biomass can be processed into a biodiesel that can be used in higher efficiency compression-ignition engines further ameliorating the effects of modern energy consumption on Earth's climate. The photobioreactor includes a fluidly interconnected circuit optimized for photosynthesis and is designed to be compatible with low-voltage, high intensity light emitting diodes (LEDs) that require limited electrical power and that are highly efficient. The generally vertical helically shaped fluidic pathway is configured to provide a high surface to volume (S/V) ratio, thereby increasing the incident light energy input per unit volume with reduced algae self-shadowing. The photobioreactor disclosed herein allows for relatively easy control of the system temperature and microbial contaminants. Further, the system can be expanded into practice such that it is efficient on a large production scale without losing efficacy and without requiring significant ground surface area that might displace crops or pastures. Large-scale systems can implemented in an environment that is insulated from harsh elements such as extreme weather and contaminants thereby allowing the algae used in the photobioreactor disclosed herein to be chosen based on efficacy in a narrower range of operating conditions.

DETAILED DESCRIPTION

These and other benefits may become clearer upon making a thorough review and study of the following detailed description. Referring now to the drawings, and in particular to FIG. 1, a photobioreactor 100 for use in treating polluted air and producing biomass is illustrated. The photobioreactor 100 may comprise, at least in part, a generally vertical tube or fluidic pathway 102, a generally vertical helically shaped tube or fluidic pathway 104 having a light source 106 position within the generally vertical helically shaped fluidic pathway 104, a head cap assembly 108, and a base assembly 110. A removable cover 114 may be positioned around the outside of the generally vertical helically shaped fluidic pathway 104 and the light source 106. By one approach, the removable cover 114 includes a reflective interior to reflect the light emitted by the light source 106 back toward the generally vertical helically shaped fluidic pathway 104. In one illustrative example, the light source 106 may be a light emitting diode (LED) or a plurality of light emitting diodes (LEDs). By one approach, a gas diffusion apparatus 112 is located at the base assembly 110 adjacent the generally vertical fluidic pathway 102 to inject gas bubbles into the photobioreactor 100 at the base of the generally vertical fluidic pathway 102.

In one illustrative example, the generally vertical fluidic pathway 102 is a generally straight-walled tube that is comprised of a food grade, clear acrylic polyvinyl chloride (PVC) or other polymer, such as a polycarbonate polymer including LEXAN. The generally vertical fluidic pathway 102, in one illustration, is approximately 8 to 10 feet (2.44 to 3.05 meters) in length, between about 3 to about 7 inches (7.62 to 17.78 centimeters) in outer diameter, and has approximately a ¼ to a ½ inch (6.35 to 12.7 millimeters) thick wall. As used herein, the expression "generally vertical" may also include "substantially" vertical. By one approach, the generally vertical pathway is within 5° of being exactly perpendicular to the horizon. However, depending on the application, it is anticipated that the orientation may vary up to 45° from such perpendicularity.

As used herein, a pathway may include a tube, conduit, chamber, or other structure capable of containing and retaining gas and liquid. Further, a pathway may be designed to be connected to other structures such that the pathway is a distinct piece that is connected together with other pieces to create a fluidly interconnected circuit. By another approach, the pathway may also be a section of an apparatus of unitary construction such that the pathway is a portion of a larger integral structure.

Figure 2:
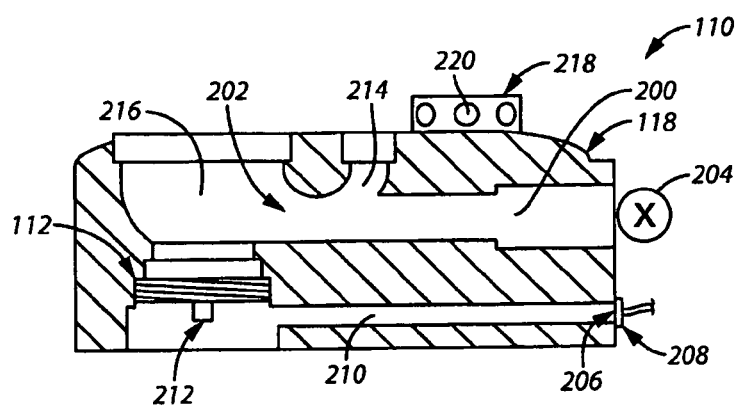
FIG. 2 comprises a front view of a portion of the photobioreactor of FIG. 1 as configured in accordance with various embodiments of the invention.

At its lower end, the generally vertical fluidic pathway 102 connects with the base assembly 110. Those persons skilled in the art will understand that a variety of connection types and methods may be used to create the fluid and air-tight seals required. Numerous examples exist in this regard and are well known to those skilled in the art. As these teachings are not particularly sensitive to any particular selections in this regard, for the sake of brevity further elaboration in this regard will not be provided here. As shown in FIG. 2, the base assembly 110 includes a water line 200 and a fluid conduit 202. As discussed in more detail below, the fluid conduit 202 connects the generally vertical fluidic pathway 102 to the generally vertical helically shaped fluidic pathway 104. The water line 200 allows the fluid medium to be drawn from the system to harvest the biomass produced in the photobioreactor 100. When the algae or other photosynthetic material has reached a certain level within or percentage of the fluid medium, a sensor monitoring the algae density within the photobioreactor 100 communicates with a valve 204, such as a solenoid ball valve, to begin harvesting the algae by discharging the fluid medium from the photobioreactor 100.

During the harvesting, the fluid level within the photobioreactor 100 will drop. To prevent too much fluid loss the low water level monitor 116 shown in FIG. 1 limits the discharge. By one approach, approximately half of the fluid medium within the photobioreactor 100 will be discharged during algae harvesting. As suggested, the discharge occurs by drawing water from the water line 200. The water line 200 is connected to a centrifugal extractor that will separate the biomass from the fluid medium. As discussed below, after the high algae fluid is discharged, or at least partially discharged, nutrient rich water will be added to the system at the head cap assembly 108.

Returning to FIG. 2, the base assembly 110 includes a gas diffusion apparatus 112 that may inject flue gas or other polluted air into the photobioreactor 110. The gas diffusion apparatus 112 in one illustration may be a sparger. By one approach, the sparger may comprise a flat nanoporous ceramic disk through which the flue gas or other polluted air passes. In one illustrative approach, the porous openings should be between approximately 20 nm to 60 nm in size to produce relatively small bubbles that may promote better gas exchange and may keep the algae better suspended in the fluid medium. The location of the diffusion apparatus 112 at the base of the generally vertical fluidic pathway 102 allows the gas to rise through the pathway 102 providing upward momentum to the flow of algae and water thereby employing a gas-lift or air lift flow as understood in the art.

As shown in illustrative FIG. 2, the gas diffusion apparatus 112 is connected to the air inlet 206 having a flow monitor 208. The air inlet 206 connects to a gas line 210 that delivers gas to the gas diffusion apparatus 112. Opposite the air inlet 206, the gas line 210 has a connection 212 to the gas diffusion apparatus 112. In one illustrative example, the gas line 210 may have an access opening with tubing that connects the flow monitor 208 to the connection 212 of the gas diffusion apparatus 112. By one approach, the gas diffusion apparatus 112 may include threads to which other portions of the gas diffusion apparatus 112, such as the sparger or ceramic disk, may attach. In one illustrative example, the flow monitor 208 regulates air flow into the photobioreactor 100 to a rate of between about 1 to about 4 $ft^3$/min. Such a flow rate produces a fluid movement with bubbles from the gas diffusion apparatus 112 that move up the generally vertical fluidic pathway 102 without shearing or otherwise damaging the photosynthetic material therein.

Figure 3:
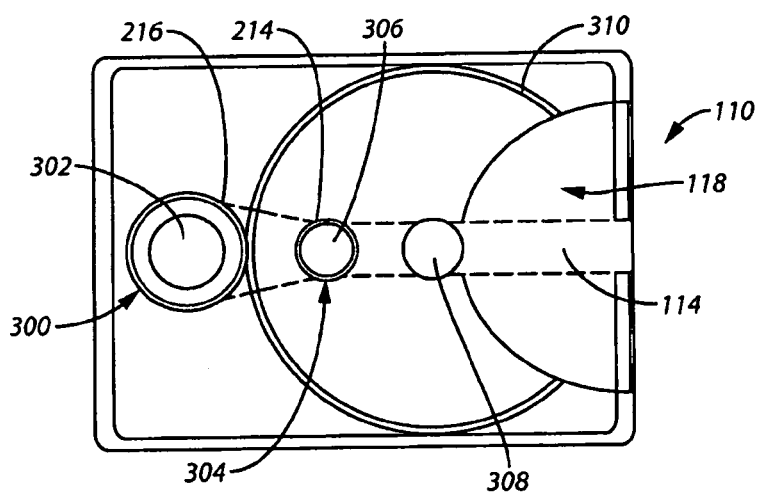
FIG. 3 comprises a top view of the portion of the photobioreactor shown in FIG. 2 as configured in accordance with various embodiments of the invention.

The fluid movement within the fluidly interconnected circuit is also affected by the venturi effect created at the base assembly 110. As shown in FIGS. 2 and 3, the fluid conduit 202 features an expanding cross section; in particular, the fluid conduit 202 includes a smaller diameter portion 214 and a larger diameter portion 216. The smaller diameter portion 214 connects to the generally vertical helically shaped fluidic pathway 104 and the larger diameter portion 216 connects to the larger diameter generally vertical fluidic pathway 102. The expanding diameter accommodates the difference in the diameters of the fluid pathways 102, 104 so that the pathways 102, 104 are fluidly interconnected. As the fluid moves down through the generally vertical helical pathway 104 into the small diameter portion 214, then into a tube with an expanding diameter, a corresponding venturi effect begins to affect the fluid velocity so as the fluid conduit 202 expands to the larger diameter portion 216 the gas diffusion apparatus 112 begins to have a more significant affect on fluid movement.

As shown in FIG. 3, the base assembly 110 may include a connecting structure 300 to accept and support the lower end of the generally vertical pathway 102 and an inlet 302, thereby allowing fluid to move into the generally vertical pathway 102. In addition, the base assembly 110 may include a connecting structure 304 to accept and support the lower end of the generally vertical helical pathway 104 and an exit 306 to allow fluid to exit from the generally vertical helical pathway 104. The connecting structure 300, 304 may include cutouts or depressions in the base along with threads, caps, seals, and the like, to note but a few.

FIG. 3 further illustrates an opening 308 for receiving the supporting structure for the light source 106 as described below. The base assembly 110 also includes a depression 310 to accept and support the removable cover 114. As shown in both FIGS. 2 and 4, the base assembly 110 includes a sloped shoulder 118 that creates an opening 120 between the removable cover 114 and the base assembly 108 such that air is allowed to pass through and dissipate some of the heat that may be generated. As shown in FIG. 2, the sloped shoulder 118 intersects with the depression 310 for the removable cover 114. As discussed later, the sloped shoulder 118 may also allow air to flow into a heat sink 900 within the light source 106.

By one approach, the base assembly 110 may be comprised of a plurality of parts, or by another approach, may be formed integrally having a one-piece construction forming the components. Further, the base assembly 110 may be distinct from both of the fluidic pathways 102, 104 or may be integral to one or both of the fluidic pathways 102, 104.

Figure 4:
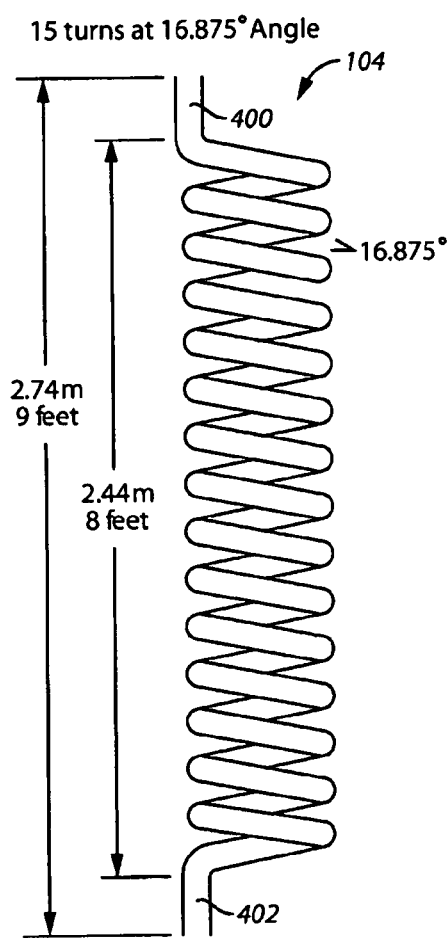
FIG. 4 comprises a side view of a portion of the photobioreactor of FIG. 1 as configured in accordance with various embodiments of the invention.
Figure 5:
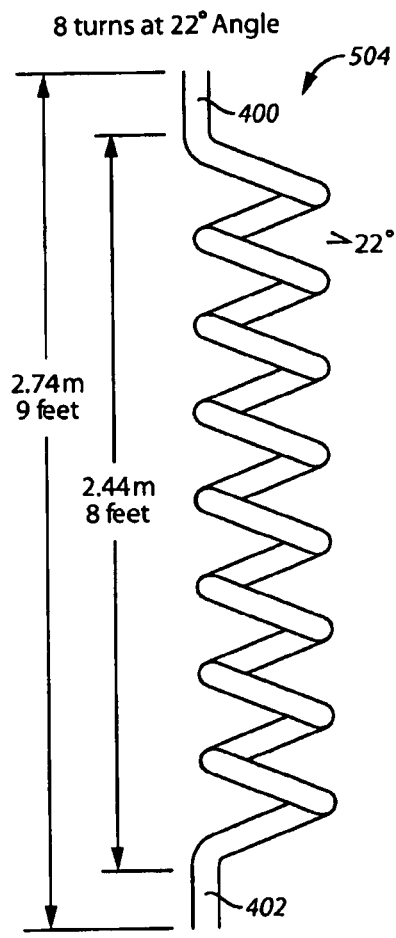
FIG. 5 comprises a side view of another embodiment of the portion of the photobioreactor shown in FIG. 4 as configured in accordance with various embodiments of the invention.

The generally vertical helically shaped fluidic pathway 104 has a twisted or coil shape that may be comprised of glass or a clear polymer. As shown in FIGS. 4 and 5, the generally vertical helically shaped fluidic pathway 104 may be approximately 8 to 10 feet in length. Further, the generally vertical helically shaped fluidic pathway 104 may have a wall thickness of between approximately ⅛ to ½ inch, a pathway diameter between about 1.0 to about 4.0 inches, and a helical diameter of between approximately 4 and 16 inches. In the illustrative embodiment of FIG. 6, the fluidic pathway 104 has a wall thickness of approximately ¼ inch, a diameter of 3 inches, a helical diameter is 6 inches, and an outer helical diameter is 12 inches. By another approach, the fluidic pathway 104 a helical diameter of 12 inches and an outer helical diameter of 18 inches.

Figure 8:
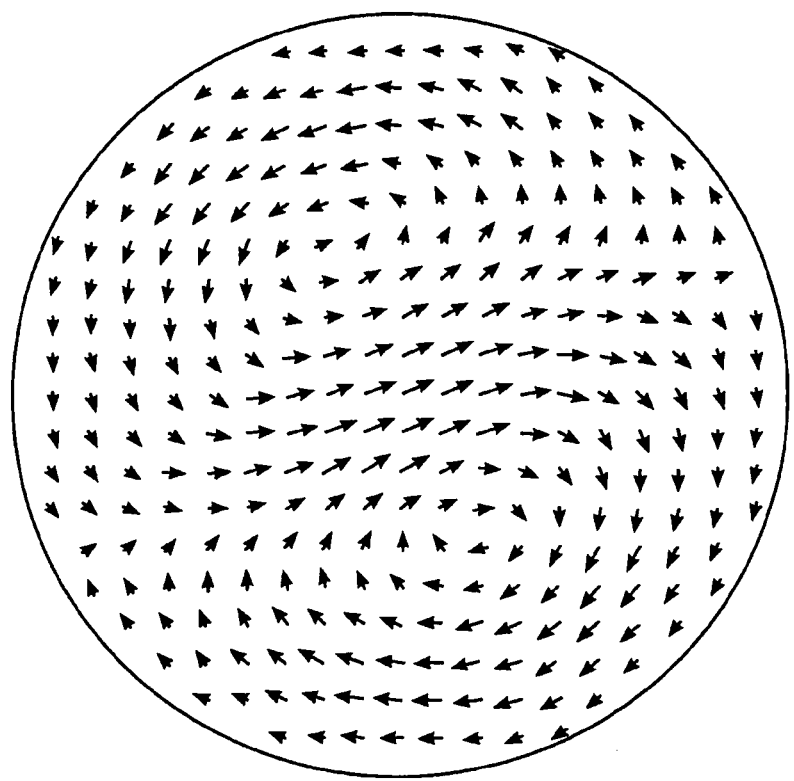
FIG. 8 comprises a flow pattern diagram as configured with various embodiments of the invention.
Figure 9:
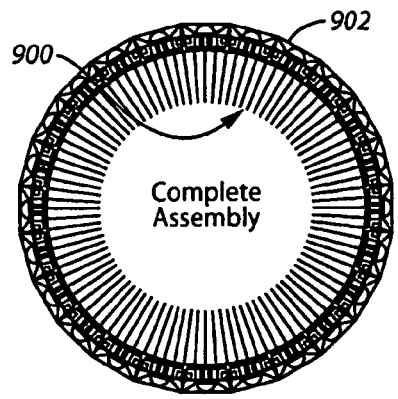
FIG. 9 comprises a top view of a portion of the photobioreactor of FIG. 1 as configured in accordance with various embodiments of the invention.
Figure 10:
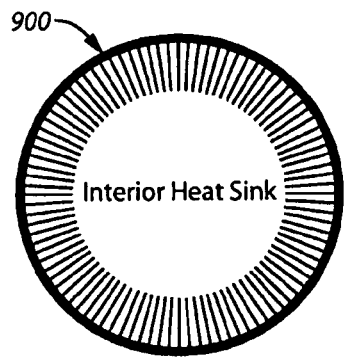
FIG. 10 comprises a top view of a portion of FIG. 9 as configured in accordance with various embodiments of the invention.

The fluid movement within the generally vertical helically shaped fluidic pathway 104 may have a double vortexual pattern consistent with the Dean vortex flow. This provides for adequate photomodulation or prime exposure to the light source 106 whether directly or by reflection from the removable cover 114. Fluid movement with counter rotating vortices may provide for controlled mixing of the fluid medium within the pathway and may thereby increase the algae expose to the wall surface of the pathway and, thus, photons of radiant light. By one approach, the counter rotating vortices within the flow of the generally vertical helically shaped fluidic pathway 104 create an axial velocity in the fluid that pushes the flow toward the outer wall as shown in FIG. 8. Such exposure to the wall of the generally vertical helically shaped fluidic pathway 104 can be useful because of the location of the light source 106 and the reflective material on the removable cover 114. Space between the helical turns allows light to travel from inside the generally vertical helically shaped fluidic pathway to the outside of the pathway 104, which may increase algae exposure to light energy when the light is reflecting back to the pathway 104. Relying on reflective light in this way may decrease the energy consumption requirements of the photobioreactor 100.

To promote desirable fluid movement, the helix angle should fall in a range that promotes the Dean vortices without creating unnecessary shearing on the photosynthetic organism or slowing fluid movement. By one approach, the helix angle is between about 15° and about 30°. In the illustrative embodiment of FIG. 5, the generally vertical helically shaped fluidic pathway 504 includes 15 turns and has a helix angle of 16.875°. In the illustrative embodiment of FIG. 6, the generally vertical helically shaped fluidic pathway 104 has 8 turns with a helix angle of 22°. Both of these examples of the generally vertical helically shaped fluidic pathway 104 allow illumination from the light source 106 to reach the reflective interior of the removable cover 114 to thereby reflect the light back to the generally vertical helically shaped fluidic pathway 104 and thereby exposing other portions to light.

Figure 6:
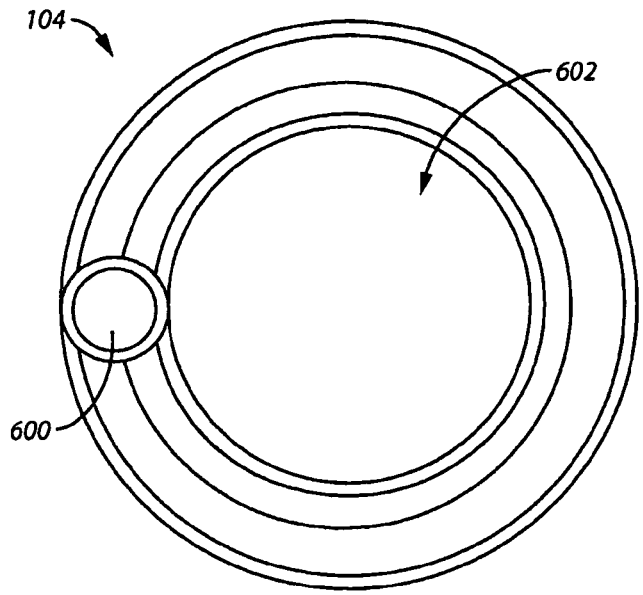
FIG. 6 comprises a top view of the portion of photobioreactor shown in FIG. 4 as configured in accordance with various embodiments of the invention.
Figure 7:
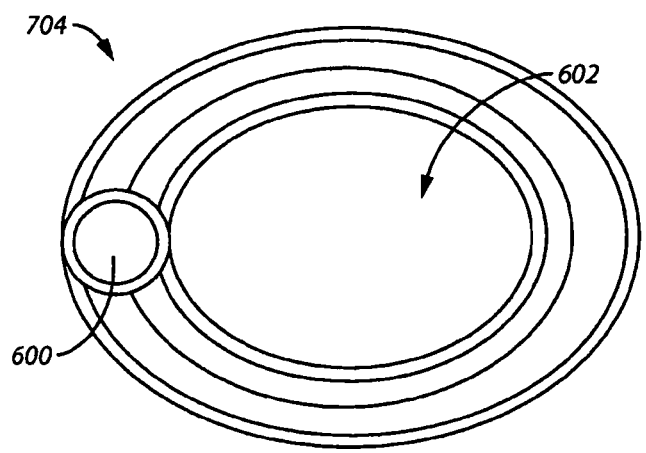
FIG. 7 comprises a top view of another embodiment of the portion of the photobioreactor shown in FIG. 6 as configured in accordance with various embodiments of the invention.

As used herein, the word "helical" may include a circular helix having substantially constant curvature and substantially constant torsion as shown in the generally vertical helically shaped fluidic pathway 104 of FIG. 6. In addition, the helical shape may not be substantially circular but may be alternatively shaped such as elliptically shaped. The generally vertical helically shaped fluidic pathway 704 shown in FIG. 7 illustrates a helix having such an elliptical profile. More particularly, the generally vertical helically shaped fluidic profile 704 has a larger diameter in one axial direction, such that the torsion is not substantially constant. In other embodiments, the helical shape may not require that each turn of the conduit be downwardly oriented or that the pathway be significantly angled. For example, the generally vertical helically shaped fluidic pathway 104 has an upper portion 400 and a lower portion 402 that are generally perpendicular to the horizon and it is contemplated that such portions perpendicular to the horizon may be positioned between angled portions of the pathway.

Returning to FIG. 6, the generally vertical helically shaped pathway 104 includes an upper and lower opening 600, one of which mates with the connecting structure 304 of the base assembly 110. The other opening 600 mates with the head cap assembly 108 discussed below.

As described above, the generally vertical helically shaped fluidic pathway 104 is vertical in that the fluid medium moving within the pathway is displaced over a vertical distance. While the generally vertical helically shaped fluidic pathway 104 includes portions that are not perpendicular to the horizon, the central axis of the pathway 104 is generally vertical in that it is aligned substantially perpendicular to the horizon. In addition, the distance over which the fluid medium is displaced may not be strictly vertical but may also include some horizontal displacement. By one approach, the generally vertical helically shaped fluidic pathway 104 is generally vertically oriented meaning that it is within 5° of being exactly vertical to the horizon, however, depending on the application, it is anticipated that the orientation may change such that the pathway is up to 45° from exactly vertical from the horizon.

Figure 11:
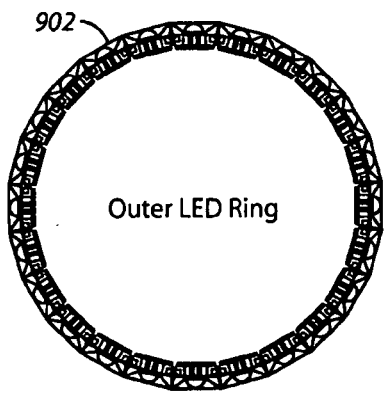
FIG. 11 comprises a top view of another portion of FIG. 9 as configured in accordance with various embodiments of the invention.
Figure 12:
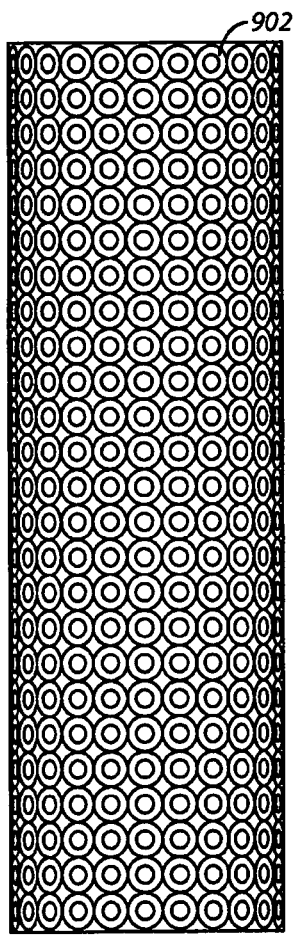
FIG. 12 comprises a front view of the portion of the photobioreactor of FIG. 11 as configured in accordance with various embodiments of the invention.
Figure 13:
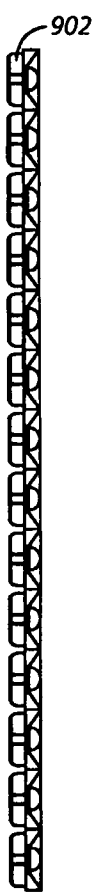
FIG. 13 comprises a side view of the portion of the photobioreactor of FIG. 11 as configured in accordance with the various embodiments of the invention.

As shown in FIG. 1, the light source 106 is positioned, at least partially, within the center of the generally vertical helically shaped fluidic pathway 104. A variety of illumination sources may be used as the photon source for the photosynthetic process. In one illustrative embodiment, the light source 106 is a low voltage direct current (DC) light source consisting of rows of specific spectrum high intensity light emitting diodes (HILEDs) 902. In addition to the light source 106, a center opening 602 of the generally vertical helically shaped fluidic pathway 104 may also include a heat exchanger or sink 900. As shown in FIG. 8, the heat sink 900 is interior to the light source 106. The light source 106 may be comprised of the HILEDs 902. The heat sink 900 may be a hollow tube upon which the light source 106 consisting of rows 904 of specific spectrum HILEDs 902 may be positioned. As shown in FIGS. 11-13, the HILEDs 902 may be closely arranged to provide for significant illumination and they may be tightly arranged around the circular curvature of the heat sink 900.

The HILEDs 902 may emit light in the 380 to 900 nm range of visible light. By one approach, the rows of specific spectrum HILEDs emitting light will be in the range of between approximately 400 nm to 700 nm. By another approach, the HILEDs 902 include a plurality of light emitting diodes between a range of 450 nm to about 680 nm. Further, in another illustrative embodiment, the HILEDs 902 include a plurality light emitting diodes in the 450 nm range, the 645 nm range, and the 660 nm range.

A variety of operating conditions may be chosen based on the photosynthetic materials used in the photobioreactor 100. For example, the light source 106 may be chosen based on how the wavelengths affect the photosynthetic materials in the system. In addition, desired system temperature may be largely dependent on the photosynthetic material's optimum environment. Thus, the heat sink 900 may be used to maintain the biological process at a constant, optimized temperature. By one approach, the heat sink 900 allows for temperature regulation to maintain the system temperature around 25° C.

In one illustrative embodiment, a lower end of the heat sink 900 connects to a mounting collar 218. The mounting collar 218 supports the lower end of the heat sink 900, which in turn supports the light source 106. As shown in FIG. 2, the mounting collar 218 has apertures 220 to allow air to enter into the heat sink 900. The base assembly 110 also includes a sloped shoulder 118 that creates an opening 120 allowing air into the removable cover 114. This opening 120 may extend toward the mounting collar 218 such that air may flow through the opening 120 and into the heat sink 900 via apertures 220.

As discussed above, the gas diffusion apparatus 112 at the base 110 allows the gas bubbles to rise, providing momentum for the upward flow of the algae and water to the top of the generally vertical fluidic pathway 102. Then, the algae and water flow back into the generally vertical helically shaped fluidic pathway 104 at the head cap assembly 108 where the gas exits and gravity moves the fluid downward through the fluidic pathway 104. This movement creates a circular flow within the photobioreactor 100.

The head cap assembly 108 connects the generally vertical fluidic pathway 102 with the generally vertical helically shaped fluidic pathway 104 opposite the base assembly 108.

The head cap assembly 108 includes a fluid conduit 1400 that has a curvature that is generally U-shaped to promote laminar flow. The fluid conduit 1400 has a larger orifice 1416 and a smaller orifice 1418. The larger orifice 1416 connects the headcap assembly 108 to the generally vertical fluidic pathway 102 and the smaller orifice 1418 connects the head cap assembly 108 to the generally vertical helically shaped fluidic pathway 104.

As mentioned, the fluid conduit 1400 of the head cap assembly 108 has curvature that is generally U-shaped. This curvature helps to maintain laminar flow of the fluid medium, minimize shearing or other unnecessary forces on the photosynthetic material, and prevent the algae from pooling in this area of the photobioreactor 100. The water level 1402 is generally above the lowest point of the generally U-shaped fluid conduit 1400 during steady state operation when the algae is not being drawn from the photobioreactor for harvesting. With the water level above the lowest point, the fluid may move to the other side of the photobioreactor 100 where the flow, being affected by gravity, begins its downward movement through the generally vertical helically shaped fluidic pathway 104.

The head cap assembly 108 may further comprises a water level monitor 1404 and water monitor probes 1406. The water supply line 1408 and a pump 1410 introduce water into the photobioreactor 100 as the system is brought online and after a portion of the fluid medium has exited from the system for harvesting of the photosynthetic material. The water supply line 1408 that is connected to the pump 1410 may be controlled by a solenoid valve. The water level monitor 1404 communicates with a water supply line 1408 and a pump 1410 to stop the incoming water once the water has reached a desired level.

The water in the photobioreactor 100 may be nutrient enriched water that may be supplied by a wastewater treatment plant. The treated wastewater may include secondary tertiary wastewater. The water monitor probes 1406 are used to monitor water quality. The water nutrients are monitored to ensure that their levels facilitate viability and growth of the photosynthetic organism contained within the liquid medium. For example, the probes 1406 may monitor the level of pH, the temperature, and the nutrient levels within the water, to note but a few. One of skill in the art will recognize that numerous combinations of liquid medium compositions, nutrients, and other components required or suitable to maintain optimal growth of the photosynthetic material are possible in this regard.

In addition to being in communication with the water level monitor 1404, the water supply line 1408 and pump 1410 also communicate with the low water level monitor 116. Thus, water may be added to the system when the water level in the generally vertical fluidic pathway 102 triggers the low water level monitor 116 during water discharge for the system for cleaning or harvesting.

At the top of the photobioreactor, the head cap assembly 108 may include a vent such as a one-way valve 1412. The one-way valve 1412 may release exhaust gas from the photobioreactor 100. The one-way valve 1412 allows the release of processed air that has entered the bioreactor at the base assembly 110 and traveled up the generally vertical pathway 102. While the air moves through the generally vertical pathway 102, carbon dioxide, nitrogen oxides, and other harmful emissions in the air interact with the photosynthetic material that has previously been exposed to the light source 106 as it traveled through the generally vertical helically shaped pathway 104.

Figure 14:
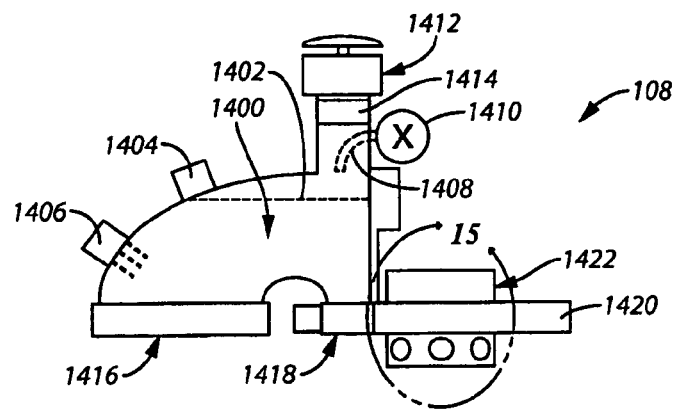
FIG. 14 comprises a front view of a portion of the photobioreactor of FIG. 1 as configured in accordance with various embodiments of the invention.

In addition to allowing processed air to exit the photobioreactor 100, the one-way valve 1412 closes as water exits from the system during algae harvesting. Such closure prevents surrounding air from entering the photobioreactor 100. As shown in FIG. 14, the head cap assembly 108 may further include a filter 1414, located below the one-way valve 1412, that may trap the algae in the system to contain renegade spores. The filter 1414 may be a sponge-type filter designed to keep the moisture in the air relatively low so as to prevent undesired evaporation.

Figure 15:
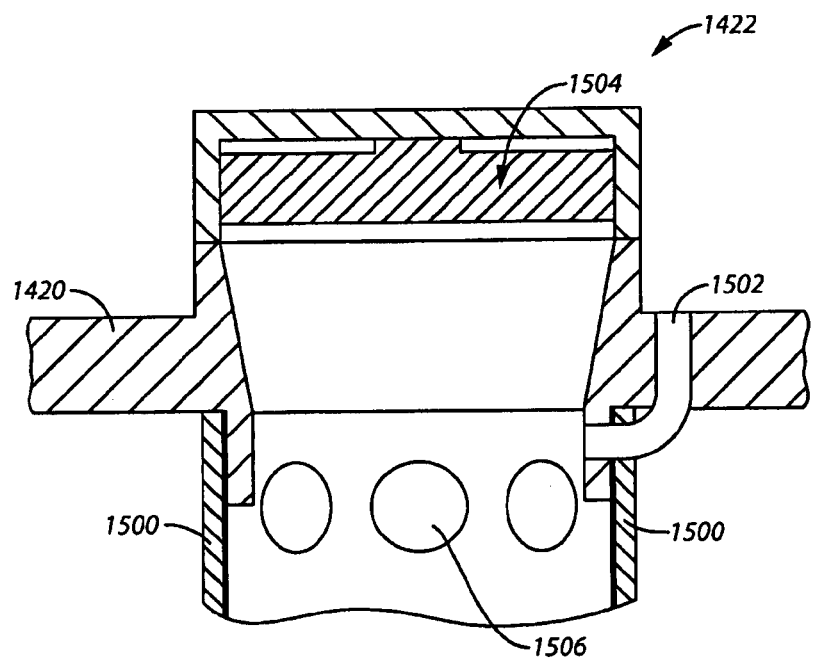
FIG. 15 comprises a cross-sectional view of a portion of FIG. 14 as configured in accordance with various embodiments of the invention.

As shown in FIG. 14, the head cap assembly 108 may include a support plate 1420 adjacent the smaller orifice 1418. The support plate 1420 may hold or support the reflective cover 114 and a housing 1422. Turning now to FIG. 15, the housing 1422 has a collar support 1500 that supports the light source 106. In the illustrative embodiment shown, the collar support 1500 mates with the heat sink 900 to which light source 106 such as the HILEDs 902 may be attached. The housing 1422 shown in FIG. 15 illustrates a wiring or cabling raceway 1502 for wire to power the light source 106, along with other wires or cables that may be used. A low voltage fan 1504 for climate control may also be located at the housing 1422. The fan 1504 may be located above the light source 106 to draw air upward through the heat sink 900 to regulate the temperature in and around the generally vertical helically shaped fluidic pathway 104. In one illustrative embodiment, the fan 1504 may comprise a low voltage 80 mm fan that draws air upward through the heat sink 900 from the opening 120 created by the sloped shoulder 118. To further regulate the temperature, the collar support 1500 may have apertures 1506 to increase air flow.

By one approach, the head cap assembly 108 may be comprised of a plurality of parts, or by another approach, may be formed integrally having a one-piece construction that forms the various components. Further, the head cap assembly 108 may be distinct pieces separate from both of the fluidic pathways 102, 104, or may be integral to one or both of the fluidic pathways 102, 104.

The photosynthetic material used within the photobioreactor 100 should be chosen based on the desired output and likely operating conditions. The photosynthetic material should be efficient at converting electromagnetic radiation into chemical energy, thus a variety of algae may be desirable including green, blue-green, or red algae, to note but a few. For example, the photosynthetic material may be comprised of *Botryococcus braunii, Euglena gracilis, Dunaliella tertiolecta, Isochrysis galbana, Nannochloris* sp., *Neochloris oleoabundans, Nannochloropsis salina, Phaeodactylum tricornutum, Pleurochrysis, Prymnesium parvum, Scenedesmus dimorphus, Spirulina* species, *Tetraselmis*, and *Tetraselmis suecica*, to note but a few. In one illustrative example, *Chlorella Pyrenoidosa* Alga has shown to be an efficient and effective photosynthetic material. In addition, when considering an algae from which biodiesel will be produced, it can be useful to consider high lipid algae.

When the photosynthetic material, such as algae, has reached a certain predetermined level or percentage of the fluid medium, a portion of the photosynthetic materials should be withdrawn or harvested. Such harvesting or cleaning helps maintains the photobioreactor 100 in a condition of optimum operation since a fluid medium with an excessively high algae content may decrease the rate of photosynthesis as a result of limited nutrient availability and limited access to the light source 106 or self-shadowing. Continuous harvesting of the photosynthetic material and processing of the flue gas can be accomplished with the use of computer monitoring and control that communicates with the various monitors, meters, valves, and pumps. The frequency of the harvesting procedure will depend on the photosynthetic material in the photobioreactor 100 in addition to other variables such as the rate of carbon dioxide containing gas entering into the system, the nutrient levels of the fluid medium, light source illumination, and the operating temperature, to note but a few.

Depending on the targeted S/V ratio, type of photosynthetic materials, medium flow rate, medium density, light intensity, power consumption, and other factors known to one of skill in the art, the diameter and angles of the generally vertical helically shaped fluidic pathway 104, and the diameter of the generally vertical fluidic pathway 102, may be selected to provide the desired output or operation of the photobioreactor 100.

Figure 16:
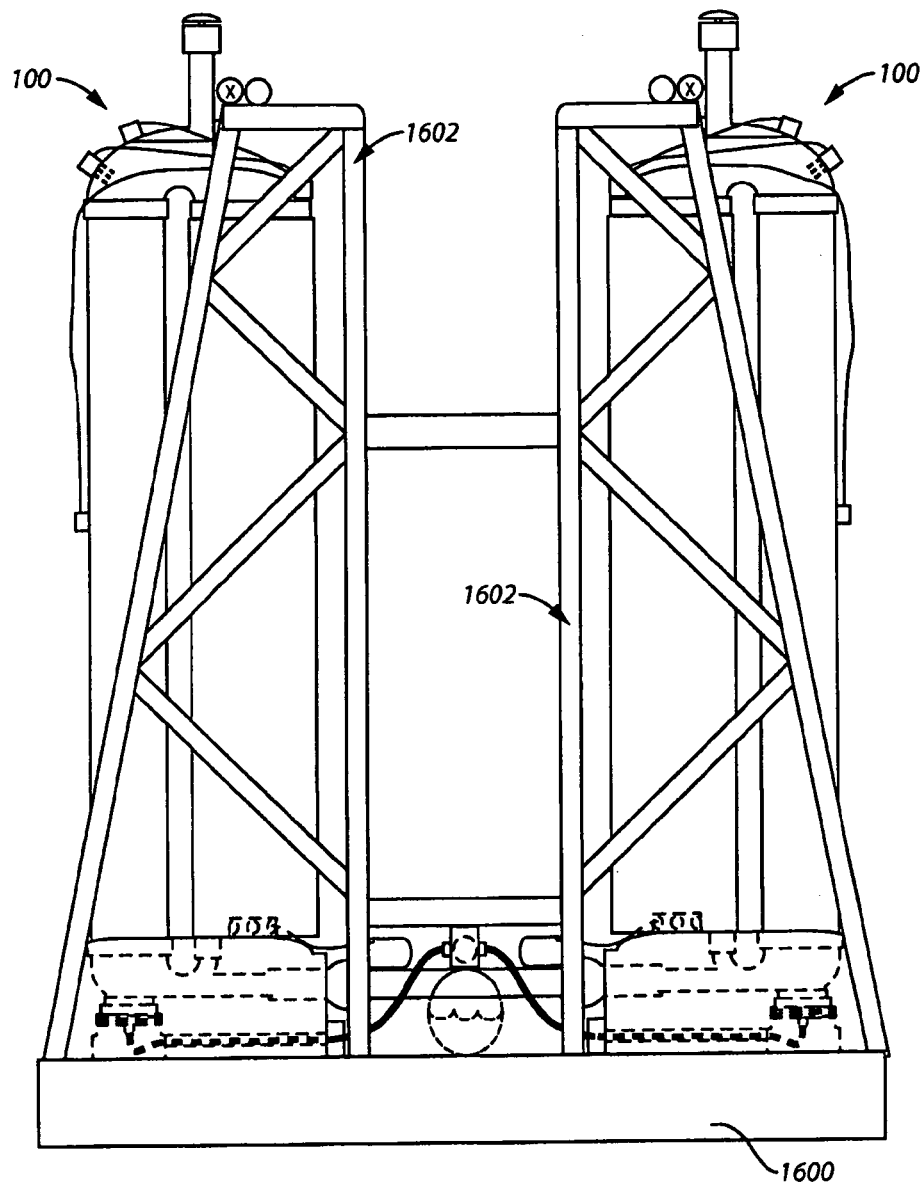
FIG. 16 comprises a front view of a rack assembly of photobioreactors as configured in accordance with various embodiments of the invention.
Figure 17:
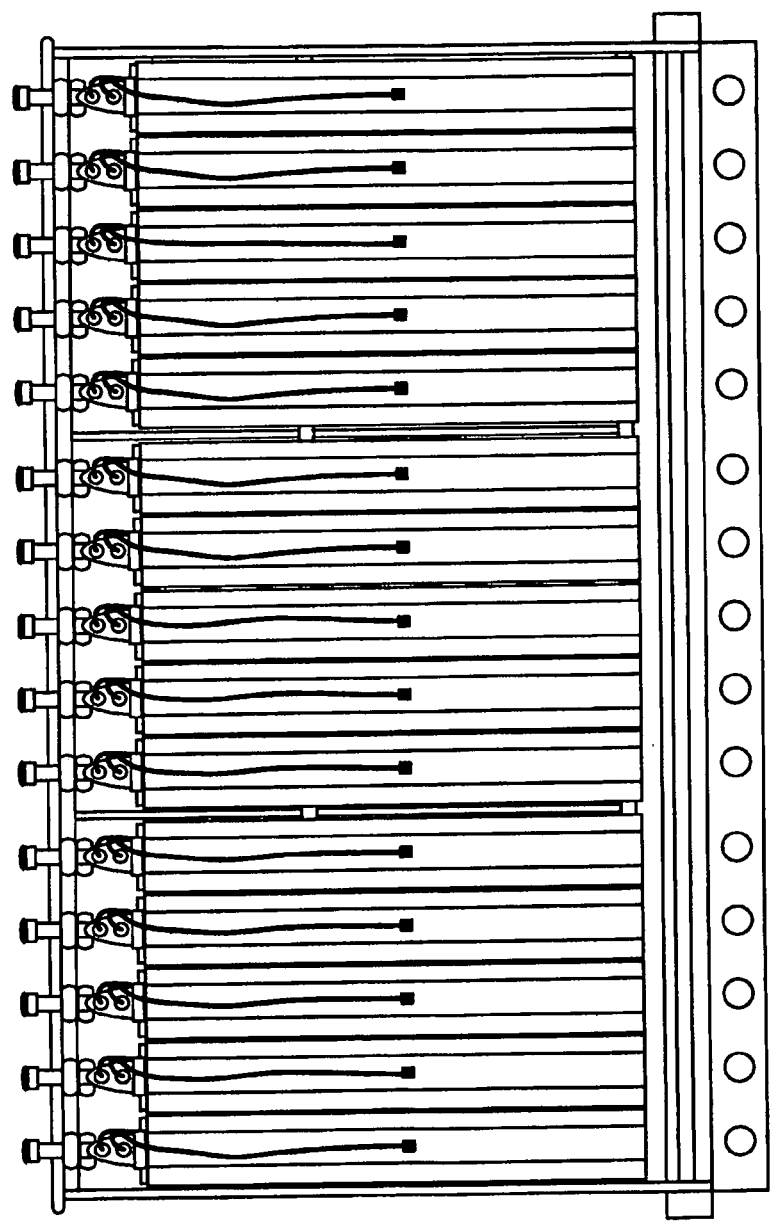
FIG. 17 comprises a side view of the rack assembly of FIG. 16 as configured in accordance with various embodiments of the invention.
Figure 18:
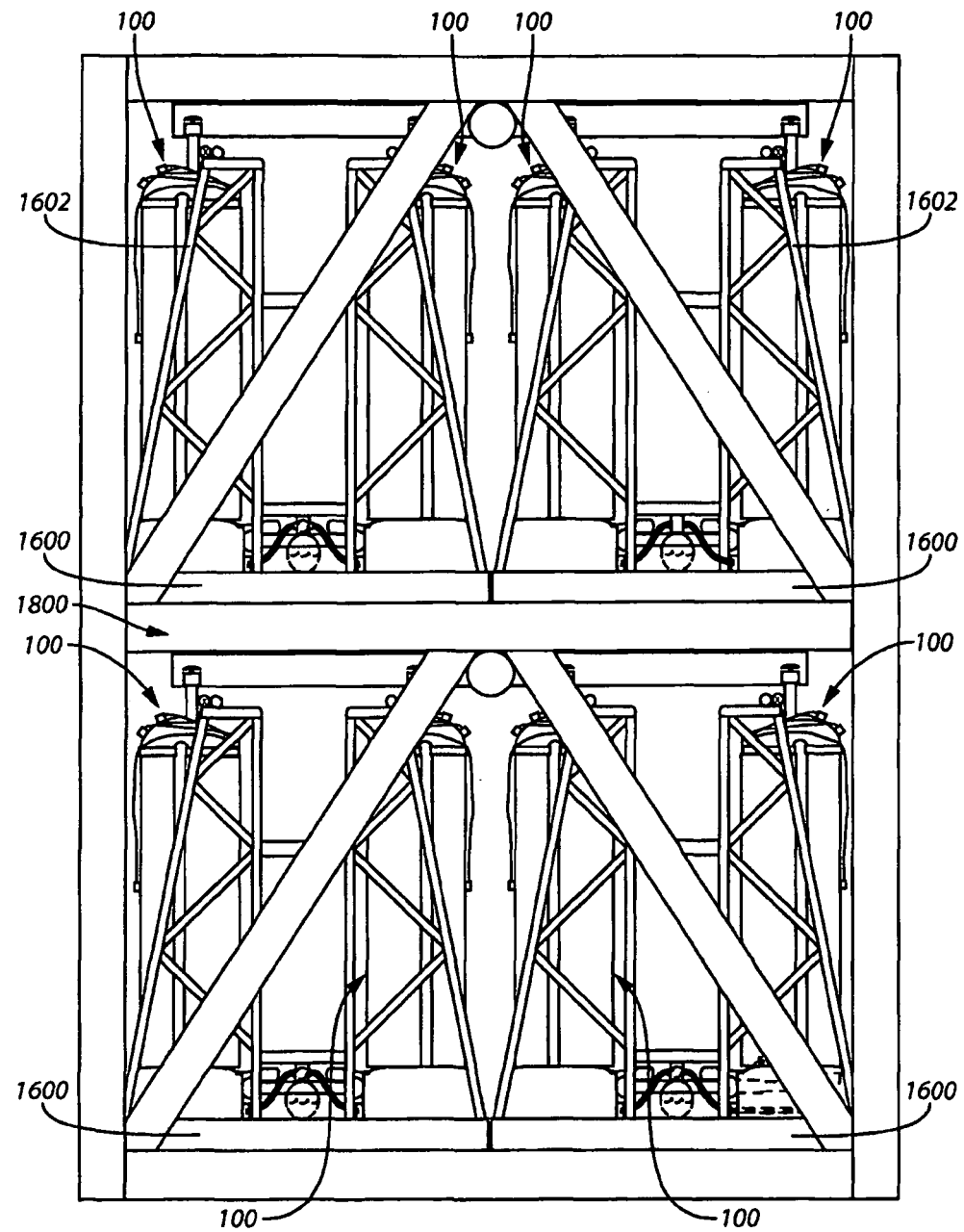
FIG. 18 comprises a front view of a rack assembly of photobioreactors stacked upon one another as configured with various embodiments of the invention.

When using the photobioreactor 100 to process a significant quantity of polluted air such as that emitted by coal burning power plants, a number of the photobioreactor units 100 will likely be required. As shown in FIG. 16, a platform 1600 can be used to support a plurality of photobioreactors 100 and the pipelines, pumps, and circuitry connected thereto. The platform 1600 may have supporting structure 1602 to hold the photobioreactor 100 in a rack assembly. FIG. 17 illustrates a plurality of photobioreactors 100 arranged back to back in another rack assembly. By one approach, the total footprint of a rack assembly is approximately 280 square feet (8 feet by 35 feet) and this rack assembly may accommodate 30 photobioreactors. These rack assemblies can then be stacked, unlike solar reactors, thereby allowing doubling or tripling of the yield per acre, depending on how high the rack assemblies are stacked. As shown in FIG. 18, the photobioreactors 100 in the platforms 1600 may be arranged or stacked one above another in a frame 1800 that supports the multiple levels of photobioreactors 100. Thus, compared with open pond systems, the photobioreactors 100 may be compacted to use less ground surface area. Further, such a system may be built in an insulated environment such as within an insulated building since solar light is not required.

Those skilled in the art will recognize that a wide variety of modifications, alterations, and combinations can be made with respect to the above described embodiments without departing from the spirit and scope of the invention, and that such modifications, alterations, and combinations are to be viewed as being within the ambit of the inventive concept.

I claim:

1. A photobioreactor comprising:
   a) a generally vertical fluidic pathway;
   b) a generally vertical helically shaped fluidic pathway winding around a central core structure, the generally vertical helically shaped fluidic pathway disposed adjacent to the generally vertical fluidic pathway;
   c) a head cap assembly fluidly connecting a first end of the generally vertical fluidic pathway with a first end of the generally vertical helically shaped fluidic pathway;
   d) a base assembly fluidly connecting a second end of the generally vertical fluidic pathway with a second end of the generally vertical helically shaped fluidic pathway; such that a biologically active material is able to move fluidly, without substantial impediment, back and forth between the generally vertical fluidic pathway and the generally vertical helically shaped fluidic pathway; and
   e) a light source at least partially disposed within the central core structure of the generally vertical helically shaped fluidic pathway wherein the generally vertical helically shaped fluidic pathway winds about the light source.

2. The photobioreactor of claim 1, wherein the light source comprises one or more light emitting diodes.

3. The photobioreactor of claim 2, wherein the light source comprises a plurality of light emitting diodes.

4. The photobioreactor of claim 3 wherein the plurality of light emitting diodes comprises light emitting diodes emitting a wavelength of light between about 400 nm and about 700 nm.

5. The photobioreactor of claim 1, wherein the light source is partially or fully coextensive with the core structure of the generally vertical helically shaped fluidic pathway.

6. The photobioreactor of claim 1 further comprising a gas diffusion apparatus located at the second end of the generally vertical fluidic pathway.

7. The photobioreactor of claim 6 wherein the gas diffusion apparatus comprises a sparger configured to inject gas bubbles at the base assembly.

8. The photobioreactor of claim 7 wherein the injected gas bubbles create a fluid movement within the photobioreactor that moves upward through the generally vertical fluidic pathway and downward through the generally vertical helically shaped fluidic pathway.

9. The photobioreactor of claim 8 wherein the downward fluid movement through the generally vertical helically shaped fluidic pathway creates a Dean vortex flow.

10. The photobioreactor of claim 1 wherein the generally vertical fluidic pathway comprises a larger diameter pathway than a diameter of the generally vertical helically shaped fluidic pathway.

11. The photobioreactor of claim 1 wherein the generally vertical helically shaped fluidic pathway has a helix angle between about 15° to about 30°.

12. The photobioreactor of claim 11 wherein the helix angle is approximately 16°.

13. A photobioreactor comprising:
   a generally vertical fluidic pathway;
   a generally vertical helically shaped fluidic pathway adjacent to the generally vertical fluidic pathway;
   a head cap assembly fluidly connecting a first end of the generally vertical fluidic pathway with a first end of the generally vertical helically shaped fluidic pathway;
   a base assembly fluidly connecting a second end of the generally vertical fluidic pathway with a second end of the generally vertical helically shaped fluidic pathway to permit a biologically active material to move fluidly, without substantial impediment, back and forth between the generally vertical fluidic pathway and the generally vertical helically shaped fluidic pathway; and
   a gas diffusion apparatus located at the second end of the generally vertical fluidic pathway, wherein the gas diffusion apparatus comprises a sparger configured to inject gas bubbles at the base assembly and wherein the injected gas bubbles create a fluid movement within the photobioreactor that moves upward through the generally vertical fluidic pathway and downward through the generally vertical helically shaped fluidic pathway.

14. The photobioreactor of claim 13 wherein the downward fluid movement through the generally vertical helically shaped fluidic pathway creates a Dean vortex flow.

15. A photobioreactor comprising:
   a generally vertical fluidic pathway;
   a generally vertical helically shaped fluidic pathway adjacent to the generally vertical fluidic pathway;
   a head cap assembly fluidly connecting a first end of the generally vertical fluidic pathway with a first end of the generally vertical helically shaped fluidic pathway; and
   a base assembly fluidly connecting a second end of the generally vertical fluidic pathway with a second end of the generally vertical helically shaped fluidic pathway to permit a biologically active material to move fluidly, without substantial impediment, back and forth between the generally vertical fluidic pathway and the generally vertical helically shaped fluidic pathway and wherein the generally vertical helically shaped fluidic pathway has a helix angle between about 15° to about 30°.

16. The photobioreactor of claim 15 wherein the helix angle is approximately 16°.

\* \* \* \* \*